United States Patent
Hutchinson, Jr.

[11] Patent Number: 5,425,740
[45] Date of Patent: Jun. 20, 1995

[54] ENDOSCOPIC HERNIA REPAIR CLIP AND METHOD

[76] Inventor: William B. Hutchinson, Jr., 1301 20th St., Ste. 376, Santa Monica, Calif. 90404

[21] Appl. No.: 243,815

[22] Filed: May 17, 1994

[51] Int. Cl.⁶ .......................................... A61B 17/00
[52] U.S. Cl. ..................... 606/157; 606/151; 606/213; 606/215; 606/221; 227/902; 24/543
[58] Field of Search ............... 606/116, 117, 151, 157, 606/158, 213, 215, 216, 219–221; 227/902; 128/831, 843; 24/543, 545, 561, 562

[56] References Cited

U.S. PATENT DOCUMENTS

| | | | |
|---|---|---|---|
| 2,371,978 | 3/1945 | Per Ham | 606/216 |
| 2,923,760 | 2/1960 | Famely | 24/561 |
| 4,038,726 | 8/1977 | Takabayashi | 24/543 |
| 4,380,101 | 4/1983 | Joubert et al. | 24/543 |
| 4,390,019 | 6/1983 | Le Veen et al. | 606/158 |
| 4,487,205 | 12/1984 | DiGiovanni et al. | 606/158 |
| 4,602,629 | 7/1986 | Schnirman | 606/158 |
| 5,100,422 | 3/1992 | Berguer et al. | 606/151 |
| 5,176,692 | 1/1993 | Wilk et al. | 606/151 |
| 5,254,133 | 10/1993 | Seid | 606/151 |
| 5,290,217 | 3/1994 | Campos | 606/151 |

*Primary Examiner*—Stephen C. Pellegrino
*Assistant Examiner*—Jeffrey A. Schmidt
*Attorney, Agent, or Firm*—Lyon & Lyon

[57] ABSTRACT

A clip unit for hernia repair surgery has first and second arms joined at a hinge joint. A latch or hook locks the arms together after they are closed. A mesh material extends around the outside edges of the clip. In use, the clip is placed over a portion of the elevated peritoneum and then closed and locked. The mesh is fixed to the surrounding peritoneum. The clip and surgical method expedites hernia repair surgery and reduces trauma and medical costs.

17 Claims, 2 Drawing Sheets

ENDOSCOPIC HERNIA REPAIR CLIP AND METHOD

BACKGROUND OF THE INVENTION

The present invention relates to a method and clip for performing hernia repair.

Over 500,000 hernia operations are performed each year in the United States. These surgeries make up about 15% of all general surgical procedures. It can be estimated that one out of twenty men, will at some point develop a hernia, and that about 1.5% of the general population (men and women) will develop this condition. Hernia surgery is accordingly widely needed, notwithstanding its costs, discomfort, risks, etc.

Many methods have been proposed in hernia surgery. Most require approximation of the tissues under tension to close the hernial defect. Unfortunately, these methods may cause increased post-operative pain and a predisposition to hernia recurrence. Tension-free repair procedures of the hernial defect using synthetic materials such as polypropylene mesh, Dacron or polytetrafluroethylene, have more recently been employed. The hernial defect is closed with the mesh which is anchored in position with staples or sutures to the surrounding facial margin. However, properly placing and anchoring the mesh can be a technically challenging procedure for the surgeon, and requires considerable expertise and time. Accordingly, there remains a need for a simpler and more easily performed hernia repair operation.

SUMMARY OF THE INVENTION

To these ends, a clip unit for hernia repair includes a clip having a first arm and a second arm joined at a hinged joint. A hook or latch on the clip is provided to hold the first arm and second arms together, around the peritoneum. A sheet of flexible material secured to the clip may be sutured or stapled to the surrounding peritoneum. The clip and mesh may be made of synthetic materials a portion of which slowly dissolve over time following the surgery. The sheet may initially be wrapped around the clip forming a small diameter clip unit which may be preloaded and passed through a trocar for endoscopic surgery.

BRIEF DESCRIPTION OF THE DRAWINGS

In the drawings, wherein similar reference numerals denote similar elements throughout the several views.

DETAILED DESCRIPTION OF THE DRAWINGS

Figure 1:
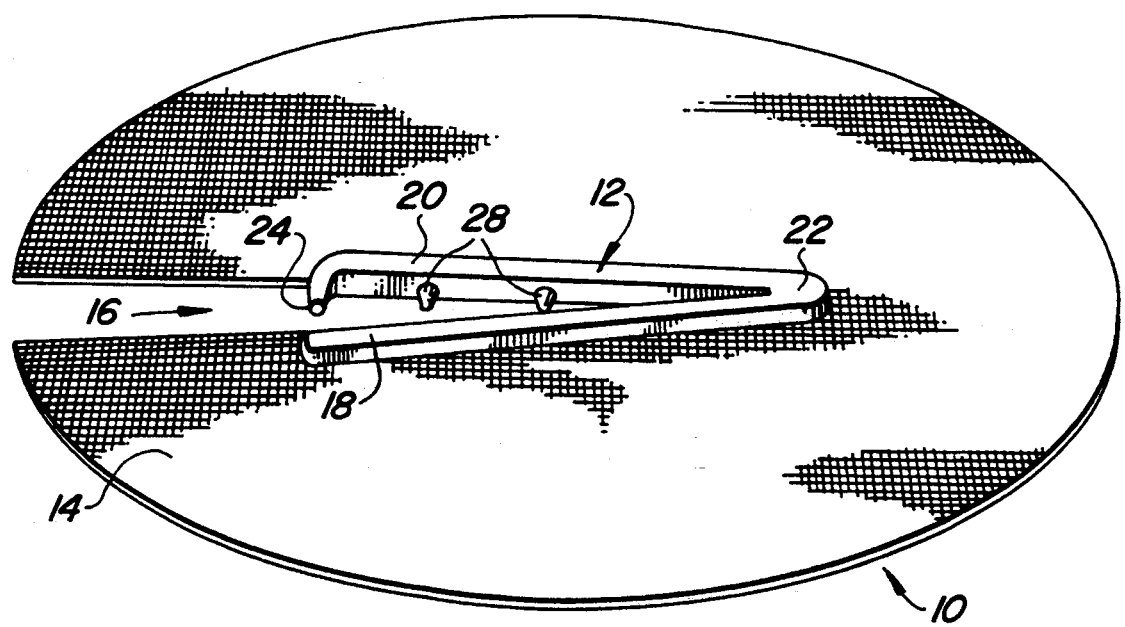
FIG. 1 is an enlarged perspective view of the present clip unit.
Figure 2:
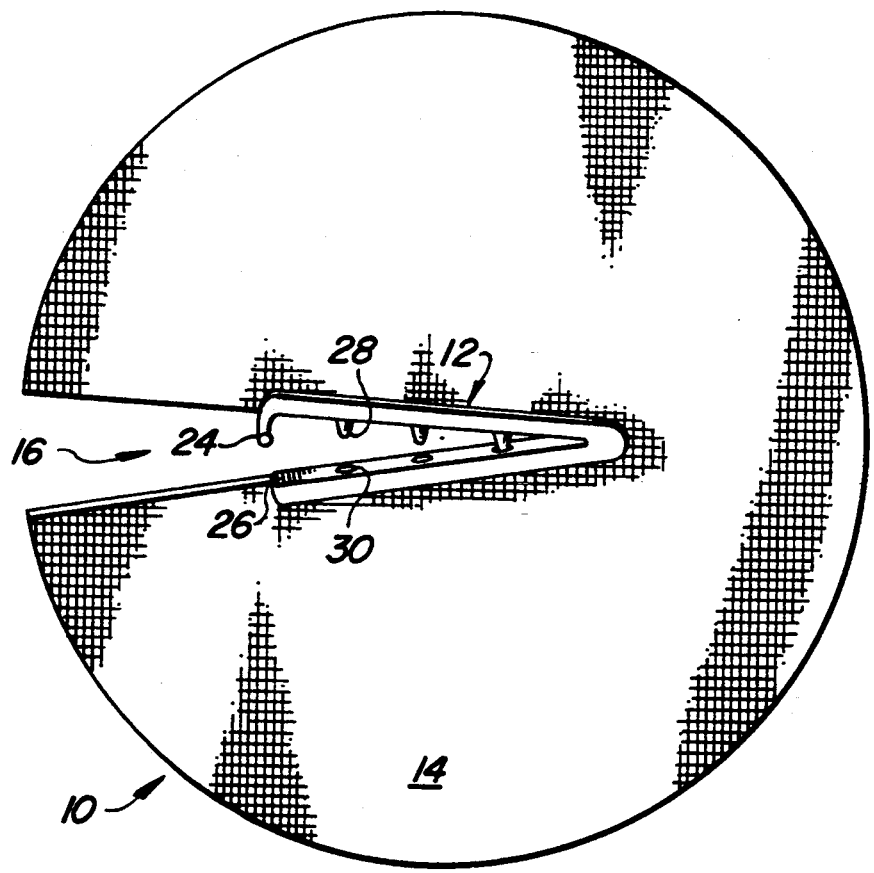
FIG. 2 is a plan view thereof.
Figure 3:
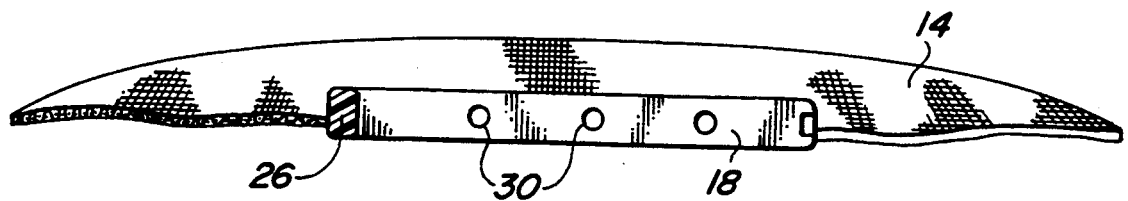
FIG. 3 is a side elevation view, in part section, showing the first arm of the clip and mesh.
Figure 4:
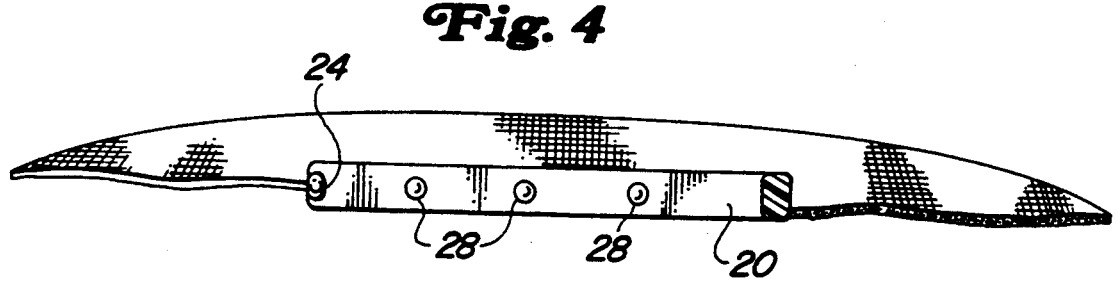
FIG. 4 is a side elevation view of the other side of the clip unit showing the second arm of the clip and mesh.

Turning now to the drawings, as shown in FIGS. 1–4, the present clip unit 10 includes a flexible sheet of material, preferably, a mesh 14, attached around the outside surface of a clip 12. The clip has a first arm 18 joined to a second arm 20 at a joint 22. A hook 24 on the second arm 20 is aligned to engage into a hook opening or latch 26 on the first arm 18. The inside surface of the second arm 20 advantageously has teeth or pins 28 which are aligned with holes 30 on the first arm 18. A slot 16 in the mesh 14 is provided when the clip 12 is open, and is sized so that the mesh will be brought together and be substantially continuous all around the clip 12 when the clip is closed. The joint 22 is advantageously a continuous hinge joint, with the flexing of the first and second arms allowing the clip 12 to be closed.

The clip 12 is preferably made of an inert biocompatible synthetic material a portion of which over time will be absorbed by the patient's body. The section of the clip over the mesh may be made of material which will dissolve over time, to reduce the bulk of the clip and potential discomfort to the patient. This upper clip section may be joined to a lower clip section below the mesh, which does not dissolve and helps to maintain the surgical repair. The clip typically ranges from 2.5–8 cm. The mesh 14 attached to the clip 12 (e.g., with adhesives or compression, molded in place, etc.) may be made of Gore-rex, Marlex, Dacron, polypropylene, polytetrafluroethylene or another suitable material. The mesh may be a composite with a top layer and bottom layer. The bottom layer, laying on the peritoneum, may be made of a mesh that the peritoneum grows into. Whereas the top layer may be inert to prevent adhesion formation. This composite would help to anchor the clip unit to the peritoneum, while avoiding having any other abdominal contents from sticking to the top surface. The mesh may be provided in a square or rectangular shape and then cut to size. The size and shape of the mesh 14 and clip 12 may be varied for different applications.

Figure 5:
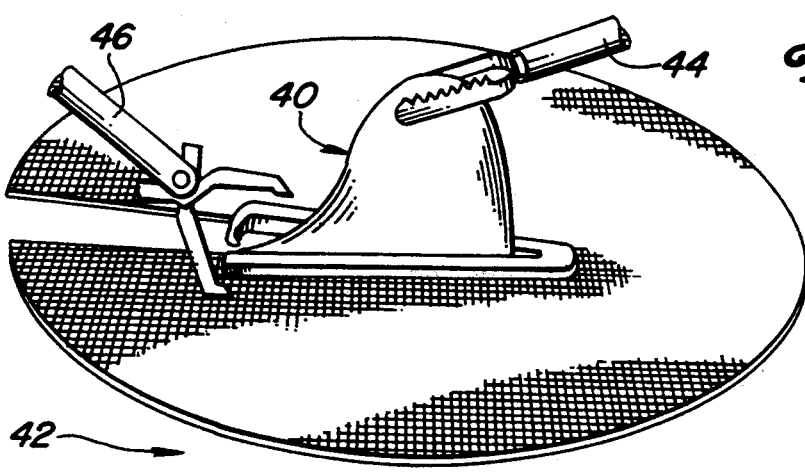
FIG. 5 is a perspective view showing the clip of FIG. 1 in use.
Figure 6:
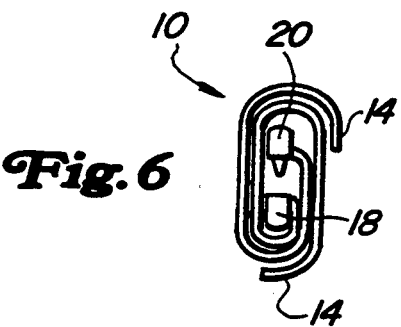
FIG. 6 is a front end view of the clip of FIG. 1 as prepared for delivery to the surgical site through a trocar.

Referring to FIGS. 5 and 6, in an endoscopic procedure, the clip unit 10 is preferably delivered to the surgical site through a cannula. The mesh 14 may be coiled or wrapped around the clip 12, as shown in FIG. 6, to provide a small diameter which may pass through the cannula. Optionally, the mesh has "memory" so that it will flatten out after it is removed from the tube.

Referring to FIG. 5, the hernia sac 40, or a portion of it is grasped with a grasper 44, and while retracted into the abdominal cavity, via the intraperitoneal approach, the clip unit 10 is placed over the elevated peritoneum 40. The clip 10 is then closed against the spring force of the arms tending to maintain them apart, and locked by squeezing the arms together, using a closing tool or grasper 46. As the arms are brought together, the hook 24 engages and locks into a hook hole or latch 26, which locks the clip into a closed position. The perimeter of the mesh 14 is then fixed to the surrounding peritoneum, e.g., with staples, sutures or other securing material. The teeth 28 extend into the holes 30 after the clip 12 is closed, and help to hold the clamped peritoneal tissue in place. The teeth fix the elevated portion of the hernia sac, and thus prevent abdominal contents from entering the sac at its neck. The peritoneum does not need to be opened, so that complications associated with it, are also reduced.

The clip unit 10 and procedure for its use reduce the time required to perform the hernia operation. In addition, trauma to the tissues in repairing an abdominal wall hernia is reduced.

Thus, although a single embodiment has been shown and described, it will be apparent to those skilled in the art that many modifications may be made thereunto without departing from the spirit and scope of the present invention.

What is claimed is:

1. A medical device for hernia repair comprising:
   a peritoneum clip having a first arm joined to a second arm, with the first and second arms each having inside and outside surfaces;
   a latch on the clip for holding the first arm and second arm together, with the inside surfaces of the first and second arms facing each other; and
   a flexible material attached to the outside surfaces of the first and second arms.

2. The medical device of claim 1 wherein the flexible material comprises a mesh.

3. The medical device of claim 1 wherein the flexible material comprises a material selected from the group consisting of polypropylene, Dacron, polytetrafluroethylene, Marlex, and Gore-rex.

4. The medical device of claim 1 further comprising at least one tooth on the first arm and at least one hole on the second arm, for receiving the tooth.

5. The medical device of claim 1 wherein the flexible material is attached substantially around the entire outside surfaces of the first and second arms.

6. The medical device of claim 1 wherein the flexible material is generally round.

7. The medical device of claim 1 wherein the arms may be flexed towards each other in a central plane, and the flexible material lies in a plane parallel to the central plane.

8. The medical device of claim 1 wherein the clip is made of biocompatible material.

9. A method of performing hernia repair surgery comprising the steps of:
   lifting the peritoneum through an opening in a clip and flexible material combination;
   closing the clip around the peritoneum, thereby positioning the flexible material relative to the peritoneum; and
   attaching the flexible material on the clip to the surrounding peritoneum.

10. The method of claim 9 further comprising the step of introducing the clip and flexible material combination to the surgical site by passing it through a cannula extending into the peritoneal cavity.

11. The method of claim 10 wherein the clip and flexible material combination are scrolled up to pass through the cannula.

12. The method of claim 9 wherein the flexible material is attached to the surrounding peritoneum with staples or sutures, and without further positioning the flexible material.

13. A hernia clip unit for hernia repair surgery, comprising:
   a clip having a first arm;
   a second arm joined to the first arm at a joint, with the first arm and second arm forming a V-shape clip;
   a flexible sheet radially extending in a plane from outside surfaces of the first arm and the second arm; and
   means for holding the free ends of the first and second arms together.

14. A device for assisting in surgical hernial repair, comprising:
   a clip having a first elongate leg and a second elongate leg joined at an acute angle to the first elongate leg; and
   a mesh material attached to the first elongate leg and the second elongate leg and extending radially outwardly therefrom, with the mesh material molded into the clip.

15. The device of claim 14 wherein the clip has an upper section on one side of the mesh material, and a lower section on the other side thereof.

16. The device of claim 14 wherein the mesh is a composite having a top layer and a bottom layer of a material different from the top layer.

17. The device of claim 16 wherein the top layer is inert to prevent adhesion formation.

* * * * *